(12) United States Patent
Kim et al.

(10) Patent No.: US 6,730,801 B2
(45) Date of Patent: May 4, 2004

(54) METHOD FOR PRODUCING DINUCLEAR TRANSITION METAL COMPLEXES AS OLEFIN POLYMERIZATION CATALYST

(75) Inventors: Eun-Il Kim, Daejeon (KR); Seung Dai Choi, Daejeon (KR)

(73) Assignee: Korea Kumho Petrochemical Co., Ltd. (KR)

( * ) Notice: Subject to any disclaimer, the term of this patent is extended or adjusted under 35 U.S.C. 154(b) by 0 days.

(21) Appl. No.: 10/316,111

(22) Filed: Dec. 11, 2002

(65) Prior Publication Data

US 2004/0054207 A1 Mar. 18, 2004

(30) Foreign Application Priority Data

Sep. 13, 2002 (KR) .................. 10-2002-0055551

(51) Int. Cl.[7] .............. C07F 17/00; C07F 7/00; C08F 4/44; B01J 31/00
(52) U.S. Cl. ............. 556/11; 556/12; 556/53; 502/103; 502/117; 526/127; 526/160; 526/943
(58) Field of Search .............. 556/11, 12, 53; 502/103, 117; 562/127, 160, 943

(56) References Cited

U.S. PATENT DOCUMENTS 5,096,867 A  3/1992  Canich ............... 556/11
5,965,758 A  10/1999  Nabika et al. ........... 502/103

FOREIGN PATENT DOCUMENTS

WO   WO 00/02891   1/2000

OTHER PUBLICATIONS

Dong–Ho Lee and Seok Kyun Noh; Polymerization with Dinuclear Metallocene Compounds, Korea Polymer Journal; Apr. 30, 2001, pp. 71–83; vol. 9., No. 2, Korea.

*Primary Examiner*—Porfirio Nazario-Gonzalez

(74) *Attorney, Agent, or Firm*—Kenyon & Kenyon

(57) ABSTRACT

The object of the present invention is to provide a method for producing a dinuclear transition metal complex of formula (1) by reacting cyclopentadienyl ligand compound of formula (2) and substituted transition metal of formula (3).

$$Cp-Si(R)_2HNANHSi(R)_2-Cp \quad \text{(Formula 2)}$$

wherein,

A represents $C_{2-30}$ alkylene, substituted alkylene, arylene, substituted arylene, cycloalkylene, substituted cycloalkylene, biarylene or substituted biarylene;

Cp represents a ligand compound having cyclopentadienyl skeleton selected from the group consisting of cyclopentadienyl, substituted cyclopentadienyl, indenyl, substituted indenyl, fluorenyl and substituted fluorenyl;

R represents $C_{1-20}$ alkyl or substituted alkyl;

H represents hydrogen atom;

Si represents silicon atom; and

N represents nitrogen atom.

$$M(NR_2')_4 \quad \text{(Formula 3)}$$

M represents transition metal of Periodic Table IV selected from titanium, zirconium and hafnium;

R' represents $C_{1-6}$ alkyl.

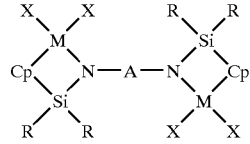

(Formula 1)

wherein,

X represents halogen atom or alkylamine; and

A, R, Si, N, Cp and M are same as defined above.

5 Claims, No Drawings

METHOD FOR PRODUCING DINUCLEAR TRANSITION METAL COMPLEXES AS OLEFIN POLYMERIZATION CATALYST

BACKGROUND OF THE INVENTION

The present invention relates to a method for producing a dinuclear transition metal complex as olefin polymerization catalyst. More particularly, the present invention a method for producing a dinuclear transition metal complex of formula (1) by reacting cyclopentadienyl ligand compound of formula (2) and substituted transition metal of formula (3).

$$Cp\text{-}Si(R)_2HNANHSi(R)_2\text{-}Cp \qquad \text{(Formula 2)}$$

wherein,

A represents $C_{2-30}$ alkylene, substituted alkylene, arylene, substituted arylene, cycloalkylene, substituted cycloalkylene, biarylene or substituted biarylene;

Cp represents a ligand compound having cyclopentadienyl skeleton selected from the group consisting of cyclopentadienyl, substituted cyclopentadienyl, indenyl, substituted indenyl, fluorenyl and substituted fluorenyl;

R represents $C_{1-20}$ alkyl or substituted alkyl;

H represents hydrogen atom;

Si represents silicon atom; and

N represents nitrogen atom.

$$M(NR_2')_4 \qquad \text{(Formula 3)}$$

M represents transition metal of Periodic Table IV selected from titanium, zirconium and hafnium;

R' represents $C_{1-6}$ alkyl.

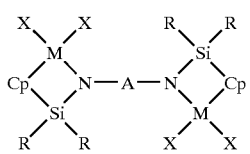

(Formula 1)

wherein,

X represents halogen atom or alkylamine; and

A, R, Si, N, Cp and M are same as defined above.

Metallocene catalyst using transition metal of Periodic Table IV has been used as an effective catalyst for various organic catalyst reactions and polymerization reactions for olefin polymer. Further, said metallocene catalyst has many merits of excellent catalytic activity and convenience for controlling molecular weight and molecular weight dispersion compared to conventional Ziegler-Natta catalyst. Among transition metal compounds of Periodic Table IV, the catalyst having cyclopentadienyl skeleton has an excellent catalytic activity and U.S. Pat. Nos. 4,584,346 and 5,965,785 disclosed that constrained geometry catalyst (CGC) having the structure of cyclopentadienyl connected with alkyl or aryl amine shows the excellent catalytic activity.

To obtain said metallocene, following process has been used. (i) Dianion is obtained by reaction of ligand and 2 mole of alkyl lithium using THF or ethyl ether as a solvent; (ii) Ligand of lithium salt is reacted with $TiCl_4(THF)_2$, $TiCl_4(Et_2O)_2$ or $ZrCl_4$ at extremely low temperature (−78° C.); (iii) The obtained product is purified and recrystallized after removing by-product, such as, LiCl. However, such process is hard to apply to the industry, because of the using solvent and the extremely low temperature.

Among various metallocene, a dinuclear transition metal complex in which two metals are contained in one compound has been developed. In *Korea Polymer Journal*, Vol. 9, No.2, pp 71–83(2001), the synthesis of dinuclear transition metal complex and its polymerization method have been disclosed. Such dinuclear transition metal complex has an excellent olefin polymerization activity, especially, the polymerization of ethylene/styrene.

In WO 00/02891, the synthesis of dinuclear transition metal complex having two cyclopentadienyl ligand is disclosed. However, said dinuclear transition metal complex also can be obtained in similar synthetic process of CGC. In detail, (i) Tetra-anion ligand is obtained by reaction of dinuclear ligand and 4 mole of alkyl lithium using THF or ethyl ether as a solvent; (ii) Dinuclear ligand of lithium salt is reacted with 2 mole of $TiCl_4(THF)_2$, $TiCl_4(Et_2O)_2$ or $ZrCl_4$ at extremely low temperature (−78° C.); (iii) The obtained product is purified and recrystallized after removing by-product, such as, LiCl. Further, in case of dinuclear metallocene, it is hard to purify or crystallize the metallocene, since two kinds of reaction compound are obtained. Therefore, according to the method in WO 00/02891, dinuclear metallocene is obtained in less than 3% yield, because dinuclear ligand having two cyclopentadienyl is used.

To overcome said drawbacks, the present invention has developed a convenient method for producing dinuclear metallocene in an industrialization scale, which also affords the high yield for preparing dinuclear metallocene by removing the hard steps of metallocene synthesis

SUMMARY OF THE INVENTION

The object of the present invention is to provide a method for producing a dinuclear transition metal complex of formula (1) by reacting cyclopentadienyl ligand compound of formula (2) and substituted transition metal of formula (3).

$$Cp\text{-}Si(R)_2HNANHSi(R)_2\text{-}Cp \qquad \text{(Formula 2)}$$

wherein,

A represents $C_{2-30}$ alkylene, substituted alkylene, arylene, substituted arylene, cycloalkylene, substituted cycloalkylene, biarylene or substituted biarylene;

Cp represents a ligand compound having cyclopentadienyl skeleton selected from the group consisting of cyclopentadienyl, substituted cyclopentadienyl, indenyl, substituted indenyl, fluorenyl and substituted fluorenyl;

R represents $C_{1-20}$ alkyl or substituted alkyl;

H represents hydrogen atom;

Si represents silicon atom; and

N represents nitrogen atom.

$$M(NR_2')_4 \qquad \text{(Formula 3)}$$

M represents transition metal of Periodic Table IV selected from titanium, zirconium and hafnium;

R' represents $C_{1-6}$ alkyl.

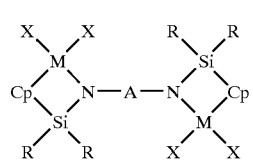

(Formula 1)

wherein,

X represents halogen atom or alkylamine; and

A, R, Si, N, Cp and M are same as defined above.

As a reaction solvent, toluene, xylene or monochlorobenzene can be used.

Further, the reaction is carried out on 20~120° C., preferably, 100~120° C.

Said substituted transition metal is one or more selected from the group consisting of $Ti(NR_2)_4$, $Zr(NR_2)_4$, $Hf(NR_2)_4$ (R is $C_{1-6}$ alkyl).

DETAILED DESCRIPTION OF THE INVENTION

In conventional method for producing metallocene compound, tetrahydrofuran (THF) or diethylether ($Et_2O$) has been used as a reaction solvent. Further, the extremely low temperature (−78 ~−40 ° C.) has to be maintained in order to react the ligand and transition metal. To maintain such extremely low temperature, highly expensive apparatus and cooling agent should be required.

On the other hand, the reactant, tetra-anion ligand has to be made after reacting dinuclear ligand and 4 mole of alkyl lithium in the presence of THF or diethylether for reacting transition metal. However, such tetra-anion ligand is very unstable in the presence of air or moisture as well as the risk of burning. Further, to obtain the dinuclear metallocene, the filtration of LiCl is required. Therefore, the yield of dinuclear metallocene has been very low.

To overcome such drawbacks in conventional method, the present invention has been accomplished.

(1) The present invention has developed the reaction solvent. Therefore, various aromatic solvent can be used in the present invention. As a preferred reaction solvent, toluene or xylene can be used.

(2) Instead of metal compound required for extremely low reaction temperature, such as $ZrCl_4$, $HfCl_4$, $TiCl_4(THF)_2$ or $TiCl_4(Et_2O)_2$, the mild metal compound of $Ti(NR_2)_4$, $Zr(NR_2)_4$ or $Hf(NR_2)_4$ (R is $C_{1-6}$ alkyl) can be used to proceed with the reaction at higher than room temperature, 20~120° C., preferably, 100~120° C.

(3) Using $Ti(NR_2)_4$, $Zr(NR_2)_4$ or $Hf(NR_2)_4$, tetra-anion ligand unstable to air or moisture is not required as a intermediate. Therefore, it is applied to industrialized scale. Further, without formation of LiCl, unnecessary filtraion process can be reduced.

(4) The reaction between dinuclear ligand and $Ti(NR_2)_4$, $Zr(NR_2)_4$ or $Hf(NR_2)_4$ can be performed in quantitative level. Therefore, the purification and recrystallization to obtain metallocene can be improved and the yield of metallocene also increases.

After $Ti(NR_2)_4$, $Zr(NR_2)_4$ or $Hf(NR_2)_4$ is reacted with the compound of formula (2) purging nitrogen gas, the compound of formula (1) is easily obtained by removing reaction byproduct, dimethylamine. At this time, the obtained compound of formula (1) has $C_{1-6}$ alkyl radical as X. Also, the compound of formula (1) has halide as X if trimethyl silylchloride is added.

The present invention can be explained more concretly by following examples. However, the scope of the present invention shall not be limited by following examples.

EXAMPLE I

Preparation of Compound of Formula (2)

Magnetic bar is laid on the 100 ml of branched round flask and nitrogen gas is purged. 1 g of 4-phenylenediamine and 50 ml of tetrahydrofuran are added as stirred and keep the temperature at 0° C. Then, 10 ml of normal buthyl lithium (2.0 mole) is added slowly and raise the temperature to the room temperature and the mixture is stirred for 1 hour. Then, 4.6 g of tetramethylcyclopentadienylsilylchloride ($Me_4CpSiMe_2Cl$) dissolved with THF is added drop by drop slowly. After adding, the mixture is stirred for 12 hours at room temperature and the solvent is removed under reduced pressure. Then, brown color solid is obtained. After dissolving solid with 100 ml of hexane, LiCl is removed using filter. Filtered solution is concentrated to 30 ml and laid on refrigerator. Then, white crystalline solid is obtained and it is washed with hexane and dried under reduced pressure. Finally, 3.1 g of the compound (m-[$(Me_4C_5H_5)Si(Me)_2(NH)]_2C_6H_4$) is obtained (yield 67%).

$^1H$ NMR ($CDCl_3$, 400 MHz) δ 6.50 (s, 4H), 3.15 (s, 2H), 2.98 (s, 2H), 1.93 (s, 12H), 1.82 (s, 12H), 1.13 (s, 12H).

EXAMPLE II

Preparation of Compound of Formula (1) (X= Alkyl)

Magnetic bar is laid on the 25 ml of branched round flask and nitrogen gas is purged. 465 mg of m-[$(Me_4C_5H_5)Si(Me)_2(NH)]_2C_6H_4$ (1 mM) and 537 mg of $Zr(NMe_2)_4$ (2 mM) and 5 ml of toluene are added and heated to 100° C. Maintaining 100° C. for about 12 hours, the mixture is stirred under nitrogen atmosphere and cooled to the room temperature. After filtration, 840 mg of brown color solid m-[$Me_2Zr(Me_4C_5H_4)Si(Me)_2(N)]_2C_6H_4$ is obtained (yield 99%).

$^1$NMR ($CDCl_3$, 400 MHz) δ 6.58 (s, 4H), 2.80 (s, 24H), 2.19 (s, 12H), 2.10 (s, 12H), 0.61 (s, 12H).

EXAMPLE III

Preparation of Compound of Formula (1) (X= Halide)

Magnetic bar is laid on the 25 ml of branched round flask and nitrogen gas is purged. 465 mg of m-[$(Me_4C_5H_5)Si(Me)_2(NH)]_2C_6H_4$ (1 mM) and 537 mg of $Zr(NMe_2)_4$ (2 mM) and 5 ml of toluene are added and heated to 100° C. Maintaining 100° C. for about 12 hours, the mixture is stirred under nitrogen atmosphere and cooled to the room temperature. Then, 0.7 ml of trimethylsilylchloride ($Me_3SiCl$) (5 mM) is added. After heating the solution up to 60° C., the mixture is stirred for 1 hour and solid is obtained. After filtering the solid and washing with hexane, 650 mg of brown color of solid m-[$Cl_2Zr(Me_4C_5H_4)Si(Me)_2(N)]_2C_6H_4$ is finally obtained under reduced pressure (yield 80.1%).

COMPARATIVE EXAMPLE

Magnetic bar is laid on the 500 ml of branched round flask and nitrogen gas is purged. 1 mg of m-[$(Me_4C_5H_5)Si(Me)_2(NH)]_2C_6H_4$ (0.025M) and 150 ml of diethylether are added and stirred to keep −78° C. Then, 71 ml of methyllithium (1.4M) is added and heated to the room temperature and stirred for 3 hours. 8.4 g of solid m-[$(Me_4C_5H_5Li)Si(Me)_2(NLi)]_2C_6H_4$ is obtained after filtering white solid and drying under reduced pressure (70.4%). Then, 4.2 g of m-[$(Me_4C_5H_5)Si(Me)_2(NH)]_2C_6H_4$ (0.0088M) is added to 200 ml of diethylether and stirred. After keeping −78° C., 5.81 g of $TiCl_4(Et_2O)_2$ (0.0172M) is added and heated to the room temperature and stirred for 12 hours. After removing the solvent under reduced pressure, the mixture is dissolved with 100 ml of pentane and filtered to remove byproduct LiCl. Filtered solution is concentrated to 30 ml and laid on refrigerator. Obtained yellow solid is filtered and washed with pentane and dried under reduced pressure. Finally, 0.45 g of m-[$Cl_2Ti(Me_4C_5H4)Si(Me)_2(N)]_2C_6H_4$ is obtained (yield 7.3%).

EXAMPLE IV

Comparison of Preparation Yield of Catalyst

The preparation yield of catalyst from same starting material m-[(Me$_4$C$_5$H$_5$)Si(Me)$_2$(NH)]$_2$C$_6$H$_4$ according to the method of example 1 and comparative example is measured and described as following table.

TABLE I

Comparison of preparation yield of catalyst

|  | yield (X = halide) |
|---|---|
| Example I | 80.1% |
| Com. Ex. I | 2.6% |

Polymerization of Ethylene

Ethylene polymerization is carried out using toluene solvent in 100 ml of reactor under present atmosphere. 45 ml of toluene is added to the reactor and keep the temperature at 60° C. 4 ml of methyl aluminoxene (11.32 mM) of cocatalyst is added and stirred for 5 minutes and m-[Cl$_2$Zr(Me$_4$C$_5$H4)Si(Me)$_2$(N)]$_2$C$_6$H$_4$ solution (18.5 μmol) of catalyst is added. Then, ethylene is injected for 1 hour. After 1 hour, the injection of ethylene is finished and mixture is poured to 200 ml of MeOH/HCl solution to stop the reaction. After drying white solid, 240 g of polyethylene (activity 13 kg mol$^{-1}$h$^{-1}$bar$^{-1}$) is obtained.

The advantageous effect of the present invention can be described as follows i) The mild of reaction temperature; ii) Without formation of tetra-anion ligand; iii) Without formation of byproduct such as lithiumchloride.

Therefore, the method of present invention can afford a dinuclear metallocene catalyst in an excellent yield and convenient process.

What is claimed is:

1. A method for producing a dinuclear transition metal complex of formula (1) by reacting cyclopentadienyl ligand compound of formula (2) and substituted transition metal of formula (3)

Cp-Si(R)$_2$HNANHSi(R)$_2$-Cp         (Formula 2)

wherein,

A represents C$_{2-30}$ alkylene, substituted alkylene, arylene, substituted arylene, cycloalkylene, substituted cycloalkylene, biarylene or substituted biarylene;

Cp represents a ligand compound having cyclopentadienyl skeleton selected from the group consisting of cyclopentadienyl, substituted cyclopentadienyl, indenyl, substituted indenyl, fluorenyl and substituted fluorenyl;

R represents C$_{1-20}$ alkyl or substituted alkyl;

H represents hydrogen atom;

Si represents silicon atom; and

N represents nitrogen atom

M(NR$_2$')$_4$         (Formula 3)

M represents transition metal of Periodic Table IV selected from titanium, zirconium and hafnium;

R' represents C$_{1-6}$ alkyl;

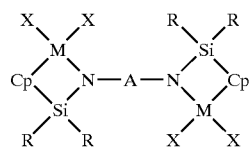
(Formula 1)

wherein,

X represents halogen atom or alkylamine; and

A, R, Si, N, Cp and M are same as defined above.

2. A method for producing a dinuclear transition metal complex of formula (1) according to claim 1, wherein said reaction solvent is toluene, xylene or monochlorobenzene.

3. A method for producing a dinuclear transition metal complex of formula (1) according to claim 1, wherein the reaction is carried out at 20~120° C.

4. A method for producing a dinuclear transition metal complex of formula (1) according to claim 1, wherein said substituted transition metal is one or more selected from the group consisting of Ti(NR$_2$)$_4$, Zr(NR$_2$)$_4$, Hf(NR$_2$)$_4$ (R is C$_{1-6}$ alkyl).

5. The method according to claim 3, wherein the reaction is carried out at 100~120° C.

* * * * *